United States Patent
Kitahara

(10) Patent No.: US 7,798,839 B2
(45) Date of Patent: Sep. 21, 2010

(54) CASING MECHANISM AND STACKED CIRCUIT BOARDS, AND MEDICAL IMAGING APPARATUS AND ULTRASOUND ENDOSCOPE USING THE SAME

(75) Inventor: Toshihiro Kitahara, Tachikawa (JP)

(73) Assignee: Olympus Medical Systems Corp., Tokyo (JP)

( * ) Notice: Subject to any disclaimer, the term of this patent is extended or adjusted under 35 U.S.C. 154(b) by 297 days.

(21) Appl. No.: 12/049,831

(22) Filed: Mar. 17, 2008

(65) Prior Publication Data
US 2008/0242981 A1 Oct. 2, 2008

(30) Foreign Application Priority Data
Mar. 30, 2007 (JP) .............................. 2007-094201

(51) Int. Cl.
*H01R 12/00* (2006.01)
(52) U.S. Cl. .................. 439/359; 361/735; 439/928
(58) Field of Classification Search ............... 439/74, 439/247, 248, 359, 928; 361/730, 735, 785, 361/796, 801
See application file for complete search history.

(56) References Cited

U.S. PATENT DOCUMENTS

| | | | | |
|---|---|---|---|---|
| 1,173,540 | A * | 2/1916 | Seeley | 331/74 |
| 3,425,025 | A * | 1/1969 | Williams | 439/347 |
| 4,200,900 | A * | 4/1980 | McGeorge | 361/803 |
| 4,546,267 | A * | 10/1985 | Urfirer | 307/116 |
| 4,945,448 | A * | 7/1990 | Bremenour et al. | 361/679.4 |
| 4,981,438 | A * | 1/1991 | Bekhiet | 439/76.1 |
| 5,057,971 | A * | 10/1991 | Hautvast et al. | 361/740 |
| 5,949,644 | A * | 9/1999 | Park | 361/679.32 |
| 6,049,452 | A * | 4/2000 | You et al. | 361/679.37 |
| 6,331,938 | B1 * | 12/2001 | Hsieh et al. | 361/735 |
| 6,370,038 | B1 * | 4/2002 | Miyake et al. | 361/814 |
| 6,450,947 | B1 | 9/2002 | Arai | |
| 6,595,786 | B2 * | 7/2003 | Horiuchi et al. | 439/74 |
| 6,663,394 | B1 | 12/2003 | Chung | |
| 6,678,140 | B2 * | 1/2004 | Jakwani et al. | 361/118 |
| 6,692,310 | B2 * | 2/2004 | Zaderej et al. | 439/701 |
| 6,796,808 | B2 * | 9/2004 | Hosoe et al. | 439/76.2 |
| 6,929,489 | B2 * | 8/2005 | Asao et al. | 439/140 |
| 2002/0197893 | A1 * | 12/2002 | Hiroyuki et al. | 439/76.2 |
| 2006/0232948 | A1 | 10/2006 | Haager et al. | |

FOREIGN PATENT DOCUMENTS

| | | |
|---|---|---|
| JP | HEI 3-16390 | 2/1991 |
| JP | 09-064566 | 3/1997 |
| JP | 2000-315877 | 11/2000 |
| JP | 2001-094273 | 4/2001 |
| JP | 3302618 | 4/2002 |
| WO | WO 02/51226 A1 | 6/2002 |

OTHER PUBLICATIONS

Japanese Office Action dated Oct. 20, 2009.

* cited by examiner

*Primary Examiner*—Neil Abrams
(74) *Attorney, Agent, or Firm*—Scully, Scott, Murphy & Presser, P.C.

(57) ABSTRACT

A casing mechanism according to the present invention includes a first connector fixedly mounted on a first circuit board; a second connector fixedly mounted on a second circuit board; and a stress absorbing member which absorbs stresses produced in the first connector and the second connector when the first circuit board and the second circuit board are fastened to a casing with the first connector and the second connector interconnected.

12 Claims, 12 Drawing Sheets

PRIOR ART

PRIOR ART

US 7,798,839 B2

CASING MECHANISM AND STACKED CIRCUIT BOARDS, AND MEDICAL IMAGING APPARATUS AND ULTRASOUND ENDOSCOPE USING THE SAME

This Application claims benefit of Japanese Application No. 2007-094201 filed in Japan on Mar. 30, 2007, the contents of which are incorporated by this reference.

BACKGROUND OF THE INVENTION

1. Field of the Invention

The present invention relates to a casing mechanism for electronic equipment and the like as well as to a medical imaging apparatus and ultrasound endoscope using the casing mechanism, where the casing mechanism contains circuit boards, board units, and the like mounted securely in a casing.

2. Description of the Related Art

Medical imaging apparatus such as ultrasound endoscope apparatus equipped with an ultrasound endoscope and the like have been put to practical use, where the ultrasound endoscope and the like is equipped, in a distal end portion of an insertion portion, with an ultrasound transducer which transmits and receives ultrasound waves and an image pickup device such as a photoelectric conversion device so that the insertion portion will be inserted in a body cavity for observation of organs and diagnosis.

Such a medical imaging apparatus contains electronic equipment made up of multiple circuit boards or board units mounted securely in a casing, where each board unit is made up of a circuit board and other relevant components. The circuit boards contain, for example, a control unit which controls driving of the ultrasound transducer, image pickup device, and the like of the ultrasound endoscope; a signal processing unit which performs various types of signal processing on an ultrasound signal, video signal, and the like received from the ultrasound endoscope; and other similar units, respectively.

As a means of electrically interconnecting multiple circuit boards in such electronic equipment, for example, a technique which interconnects the multiple circuit boards using a wire harness has been known previously.

FIG. 18 is a diagram showing an example of such a case. In FIG. 18, two circuit boards—a first circuit board 111 and second circuit board 121—are interconnected electrically by a wire harness 201 such as a flat cable.

On the other hand, as a means of electrically interconnecting multiple circuit boards without using a wire harness, a technique which uses connector members mounted on the circuit boards has been known previously.

FIG. 19 is a diagram showing an example of such a case. In FIG. 19, two circuit boards—a first circuit board 111A and second circuit board 121A—are equipped with a first connector member 114 and second connector member 124, respectively, and the two circuit boards 111A and 121A are interconnected electrically when the two connector members 114 and 124 are fitted together.

Thus, it is known that various means of connection have been available to interconnect multiple circuit boards.

However, in the case of a medical imaging apparatus such as an ultrasound endoscope apparatus, which has a large number of signal lines extending from a large number (hundreds) of ultrasound transducers and needs to ensure electrical connection of each signal line, the use of harness connection for electrical connection among the circuit boards will result in, for example, increased harness width, which may cause problems such as difficulty to form the harness and secure layout space and susceptibility to ambient noise. In particular, ultrasound signals handled by the ultrasound endoscope apparatus and the like are weak signals, which are susceptible to noise.

Thus, when electrically interconnecting multiple circuit boards and the like, a general tendency is to adopt means of connection which uses connector members to improve working efficiency and performance especially when there are a large number of connection wires.

In the case of electronic equipment in a medical imaging apparatus such as ultrasound endoscope apparatus, it is often the case that connector members are mainly used in a casing as a means of electrical connection among circuit boards as well as between circuit boards and board units.

In this case, the circuit boards, board units, and the like are configured to be replaceable by being mounted detachably in the casing. The use of connector members in interconnecting circuit boards or board units has the advantage of making attach/detach operations easier.

On the other hand, the electronic equipment in a medical imaging apparatus such as ultrasound endoscope apparatus requires a mechanism (hereinafter referred to as a casing mechanism) for screwing or otherwise fastening the circuit boards and board units in the casing. In this case, the casing mechanism generally has, for example, a sheet-metal structure.

Consequently, with the casing mechanism structured in this way, for example, depending on machining accuracy and the like, there can be misalignment between casing fasteners and board-side fastening locations (screw holes and the like) in the circuit boards which are fastened to the casing fasteners.

Also, the casing may be twisted depending on usage situations of the apparatus and external factors such as temperature changes. In that case, there can also be misalignment between the casing fasteners and board-side fastening locations.

To deal with the above situations, various measures have been proposed to absorb misalignment in the casing attributable to machining accuracy, external factors, and the like.

Now, let us consider a concrete configuration of a casing mechanism for electronic equipment in a medical imaging apparatus, where the casing mechanism is structured such as to electrically interconnect circuit boards, board units, and the like using connector members installed on the circuit boards and fasten the circuit boards and the like to casing fasteners with screws. FIG. 20 is a conceptual diagram showing a concrete example of such a case.

As shown in FIG. 20, the casing mechanism exemplified here is designed to fasten the circuit boards 111B and 121B to separate casing fasteners 131 and 132 with screws while ensuring electrical connection between two circuit boards 111B and 121B using connector members 114 and 124.

The casing mechanism configured as described above is assembled as follows. The second circuit board 121B is fastened to the second casing fastener 132, for example, at four locations using four screws 134. The second connector member 124 has been mounted on a mounting surface of the second circuit board 121B.

In this state, the first connector member 114 mounted on a mounting surface of the first circuit board 111B is fitted in the second connector member 124 of the second circuit board 121B. Consequently, the two circuit boards 111B and 121B are interconnected electrically.

In the state in which the two circuit boards 111B and 121B are interconnected via the connector members 114 and 124, the first circuit board 111B is fastened to the second circuit board 121B—which is fastened to the second casing fastener 132—only by means of the connector members 114 and 124. In this state, the first circuit board 111B is fastened to the first casing fastener 131, for example, at four locations using four screws 133.

Consequently, the first circuit board 111B is fastened to both the second circuit board 121B and first casing fastener 131.

In this way, the fit between the connector members 114 and 124 ensures electrical connection between the two circuit boards 111B and 121B while fastening the first circuit board 111B to the second circuit board 121B fastened to the casing fastener 132 in advance. Consequently, the first circuit board 111B is positioned with respect to the second circuit board 121B to begin with.

Next, in this state, the first circuit board 111B is screwed to the first casing fastener 131 to fasten the first circuit board 111B.

In the casing mechanism structured as described above, when the connector members 114 and 124 are fitted together, each fixing hole 111a formed in the first circuit board 111B and a corresponding screw hole 131a formed in the first casing fastener 131 must approximately align with each other.

However, there can be misalignment between the fixing holes 111a and screw holes 131a when the circuit board and casing are joined depending on accuracy and the like of drilling in the board and screw hole drilling in the casing.

In this case, when there is large misalignment between the fixing holes 111a and screw holes 131a, the screws 133 cannot be screwed into the screw holes 131a through the fixing holes 111a. On the other hand, when there is small misalignment between the fixing holes 111a and screw holes 131a, even if the screws 133 can be screwed into the screw holes 131a through the fixing holes 111a, loads are imposed on the fixing holes 111a, and thus on the first circuit board 111B when the screws 133 are screwed into the screw holes 131a. Consequently, loads are also imposed on the connector members 114 and 124.

Thus, by taking such misalignment into consideration, the fixing holes 111a in the first circuit board 111B fastened to the first casing fastener 131 with screws, for example, are made slightly larger in size to make some allowance.

That is, in the example shown in FIG. 20, since the fixing holes 111a are made slightly larger in diameter to make some allowance, when the screws 133 are passed through the fixing holes 111a and screwed into the screw holes 131a of the first casing fastener 131, the first circuit board 111B can be moved slightly along the mounting surface of the first circuit board 111B, i.e., in a direction perpendicular to a direction of screwing of the screws 133 until the screws 133 are tightened completely. However, since the first circuit board 111B has been fastened by means of the fit between the connector members 114 and 124, actually the first circuit board 111B cannot be moved, being fixed with respect to the second circuit board 121B as described above.

In short, the fixing holes 111a are made slightly larger to absorb misalignment between the fixing holes 111a and screw holes 131a.

In this way, the casing mechanism shown in FIG. 20 ensures stability of electrical connection between the circuit boards 111B and 121B by setting reference mounting position of the first circuit board 111B to position of the connector members (114 and 124). Also, the casing mechanism absorbs misalignment between the fixing holes 111a in the first circuit board 111B and screw holes 131a in the first casing fastener 131 by making the fixing holes 111a slightly larger in diameter, and thereby prevents application of unnecessary loads on the connector members.

With the two circuit boards 111B and 121B interconnected securely by means of the connector members 114 and 124 and with the two circuit boards 111B and 121B fastened properly to the respective casing fasteners 131 and 132, desirably components are assembled without application of unnecessary loads on the connector members 114 and 124 or the circuit board itself.

However, with conventional casing mechanisms, it is common that mounting errors are caused by misalignment between circuit boards or between circuit boards and casing fasteners as described above and various measures have been devised by taking this situation into consideration.

For example, Japanese Patent Application Laid-Open No. 2001-94273 discloses a casing mechanism which is a cylindrical unit containing circuit boards. In order to prevent application of unnecessary loads on the circuit board even if the casing is twisted due to usage situations of the apparatus and external factors such as temperature changes, the circuit boards are placed being centered at a center axis of a cylindrical shape and are held by struts made of a material which elastically deforms in response to twisting of the casing.

Also, Japanese Patent Application Laid-Open No. 2000-315877 discloses a casing mechanism, wherein reinforcement members are placed in a casing to protect circuit boards from vibrations and shocks.

Furthermore, Japanese Patent No. 3302618 discloses a casing mechanism which contains board-clamping holders made of an elastically deformable material to elastically fasten circuit boards to casing fasteners.

Consequently, even under circumstances in which the circuit boards would be get shaky due to usage situations of the apparatus and external factors such as temperature changes, elastic deformation of the board-clamping holders absorb misalignment of mounting positions between the circuit boards and casing fasteners and thereby prevents connector members from being disconnected or causing loose connections.

SUMMARY OF THE INVENTION

A casing mechanism according to the present invention includes: a first connector fixedly mounted on a first circuit board; a second connector fixedly mounted on a second circuit board; and stress absorbing means which absorbs stresses produced in the first connector and the second connector when the first circuit board and the second circuit board are fastened to a casing with the first connector and the second connector interconnected.

The above and other objects, feature and advantages of the invention will become more clearly understood from the following description referring to the accompanying drawings.

DETAILED DESCRIPTION OF THE PREFERRED EMBODIMENTS

Figure 1:
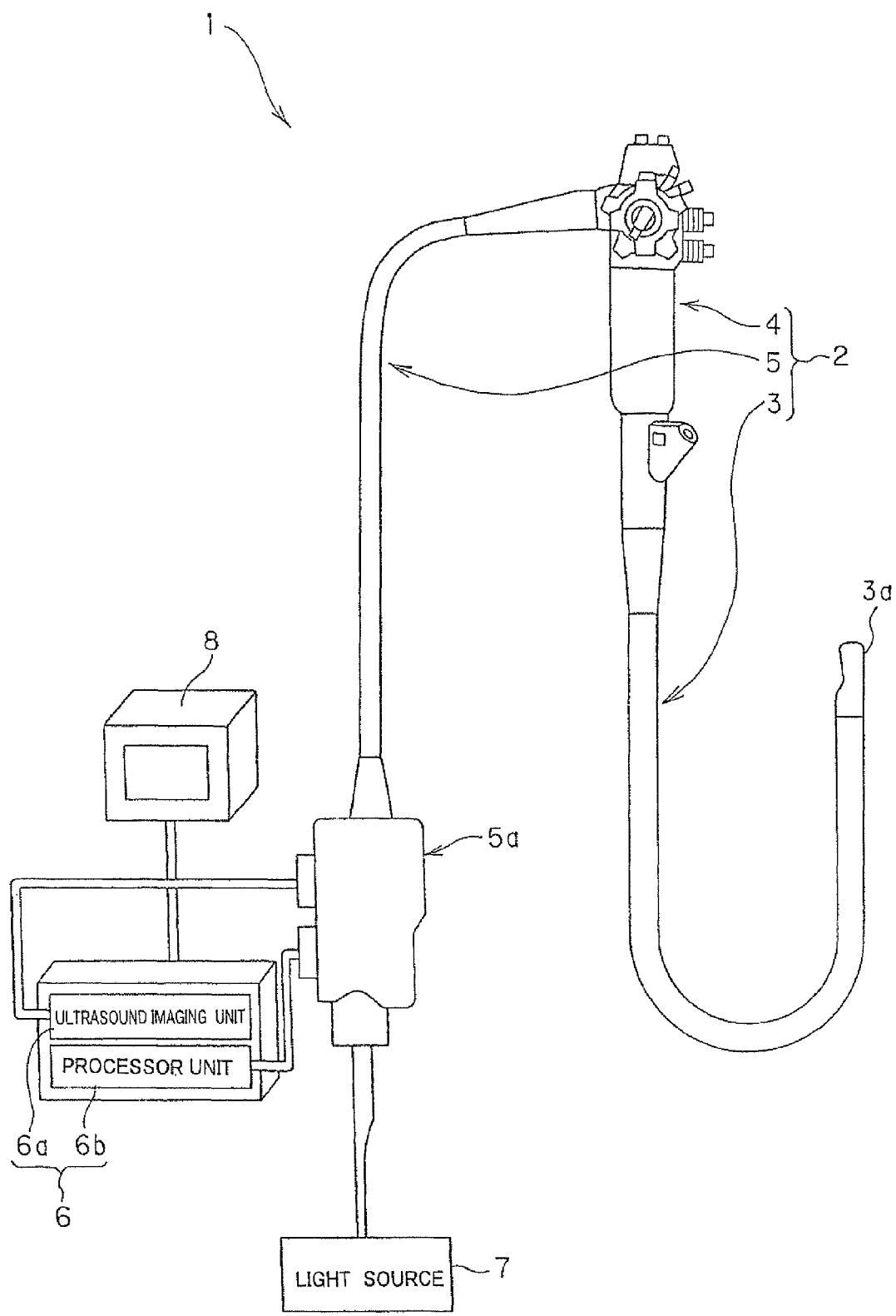
FIG. 1 is a schematic block diagram outlining an overall configuration of an ultrasound endoscope apparatus which uses a casing mechanism according to an embodiment of the present invention.

The present invention will be described below with reference to an embodiment illustrated in the drawings.

Figure 2:
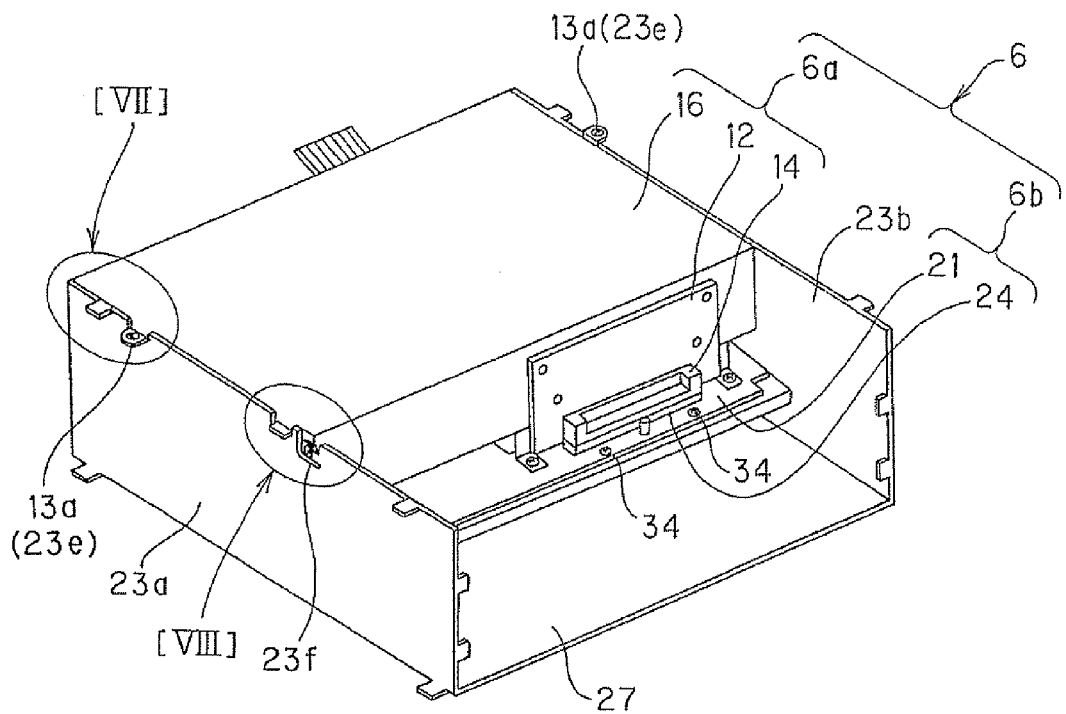
FIG. 2 is an enlarged perspective view showing principal part of a casing mechanism for a controller of the ultrasound endoscope apparatus in FIG. 1.
Figure 3:
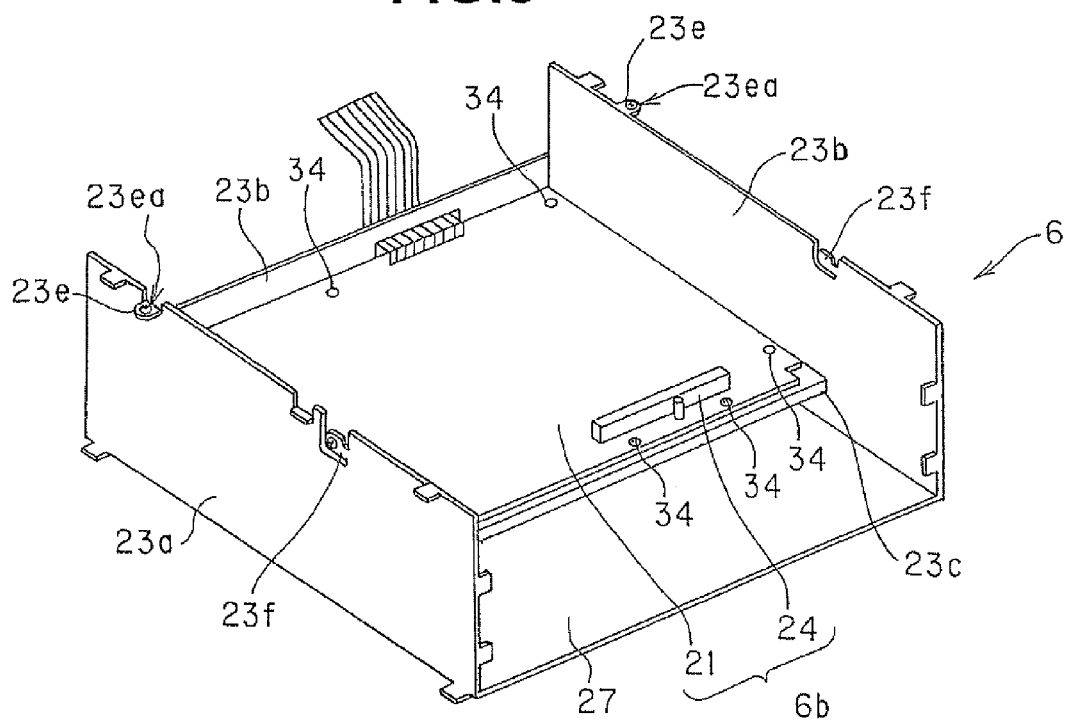
FIG. 3 is a perspective view of a part (processor unit) extracted from an internal configuration of the controller in FIG. 2.
Figure 4:
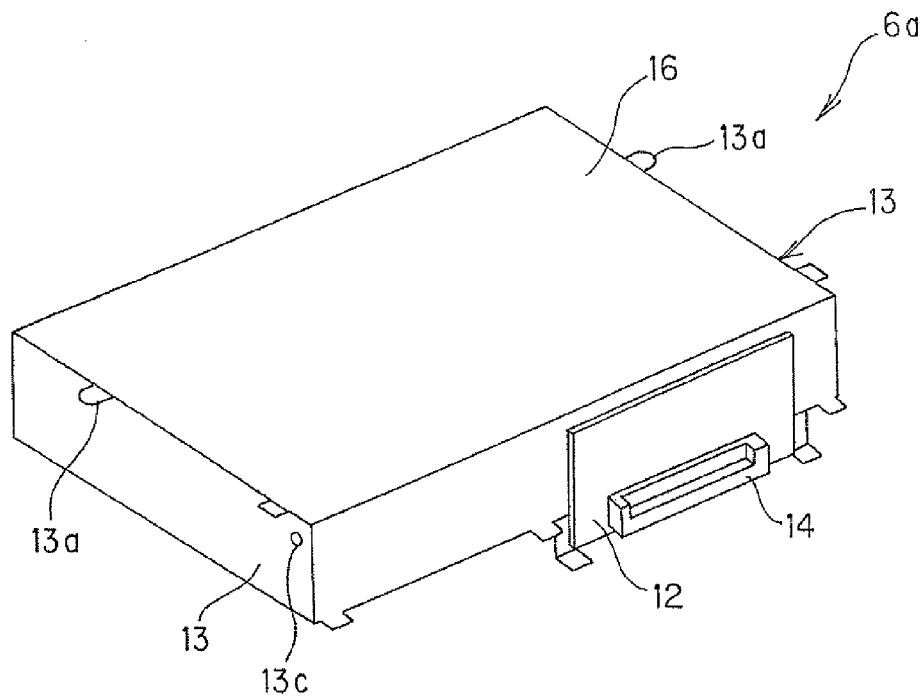
FIG. 4 is a perspective view of a part (ultrasound imaging unit) extracted from an internal configuration of the controller in FIG. 2.
Figure 5:
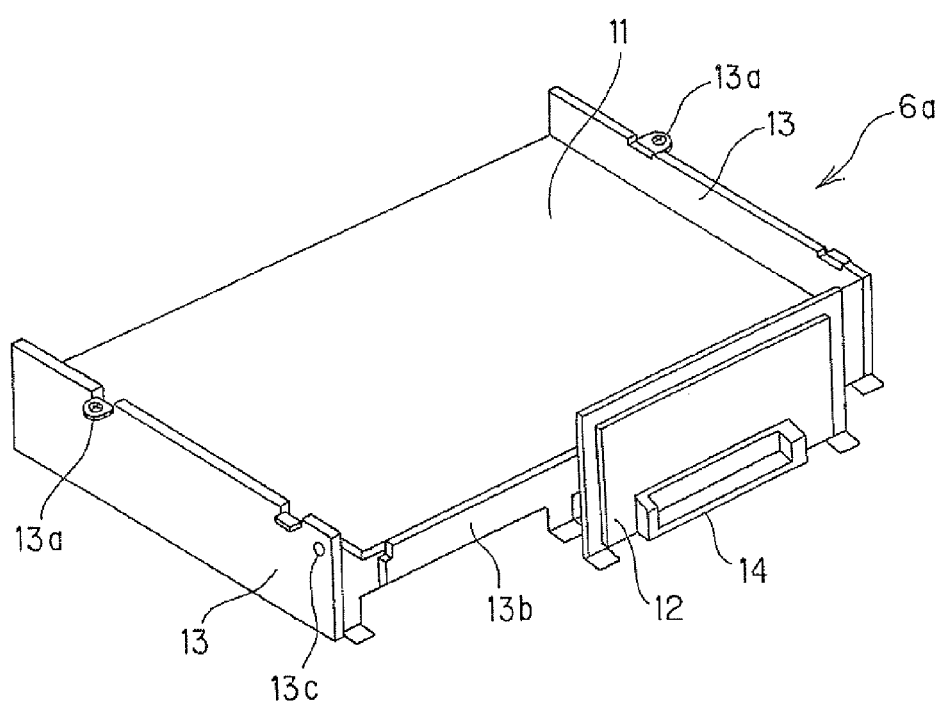
FIG. 5 is a perspective view showing an internal configuration of the ultrasound imaging unit in FIG. 4 by taking away an outer lid member.
Figure 6:
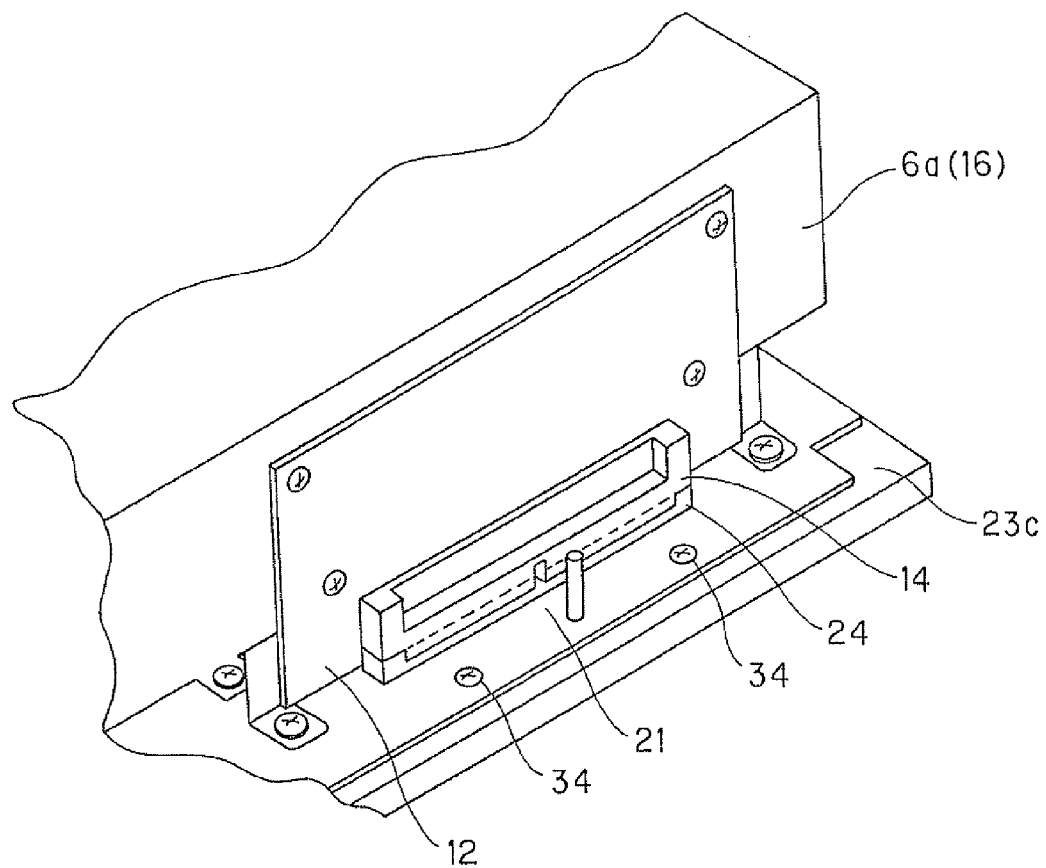
FIG. 6 is an enlarged perspective view showing principal part (near a connector member) of the controller in FIG. 2 in enlargement.
Figure 7:
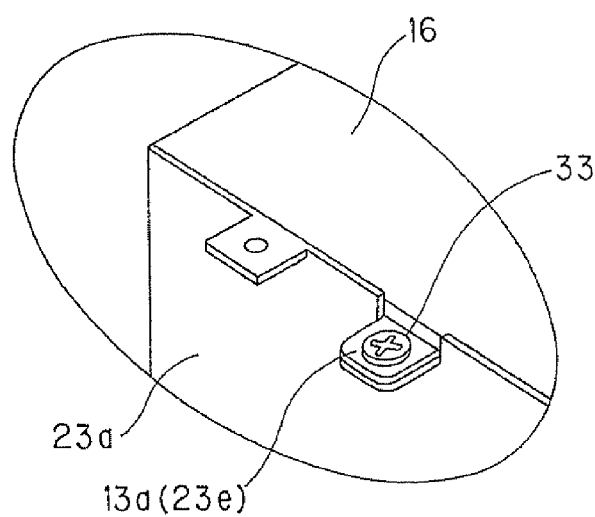
FIG. 7 is an enlarged perspective view showing principal part (near one casing fastener) of the controller in FIG. 2 in enlargement.
Figure 8:
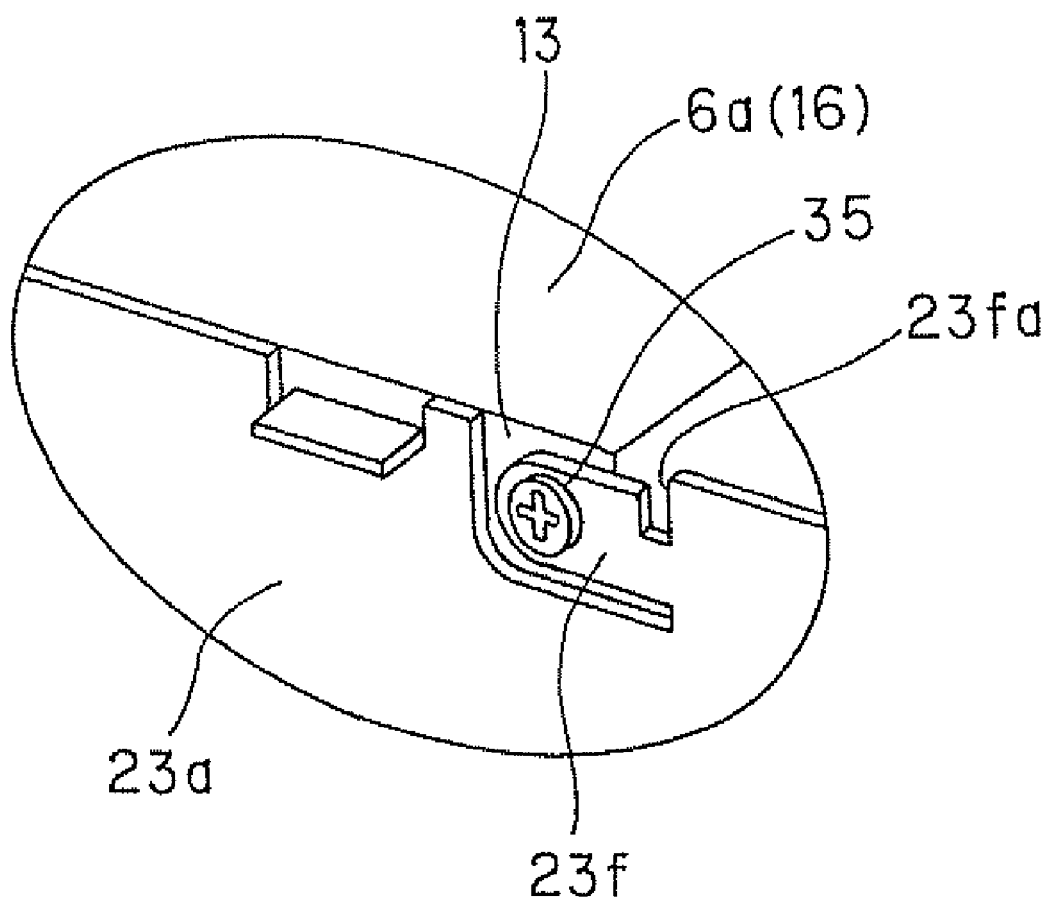
FIG. 8 is an enlarged perspective view showing principal part (near another casing fastener) of the controller in FIG. 2 in enlargement.

FIGS. 1 to 8 are diagrams showing an embodiment of the present invention. FIG. 1 is a schematic block diagram outlining an overall configuration of an ultrasound endoscope apparatus which uses a casing mechanism according to the present embodiment. FIG. 2 is an enlarged perspective view showing principal part of a casing mechanism for a controller of the ultrasound endoscope apparatus in FIG. 1. FIG. 3 is a perspective view of a part (processor unit) extracted from an internal configuration of the controller in FIG. 2. FIG. 4 is a perspective view of a part (ultrasound imaging unit) extracted from an internal configuration of the controller in FIG. 2. FIG. 5 is a perspective view showing an internal configuration of the ultrasound imaging unit in FIG. 4 by taking away an outer lid member. FIG. 6 is an enlarged perspective view showing principal part (near a connector member) of the controller in FIG. 2 in enlargement. FIG. 7 is an enlarged perspective view showing principal part (near one casing fastener) of the controller in FIG. 2 in enlargement. FIG. 8 is an enlarged perspective view showing principal part (near another casing fastener) of the controller in FIG. 2 in enlargement.

Figure 9:
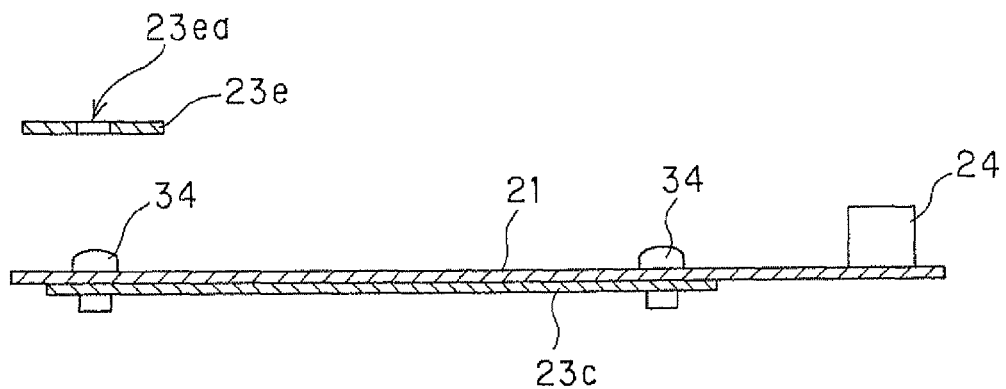
FIG. 9 is a conceptual diagram showing a cross section of one of substrate units in the casing mechanism to outline assembly procedures of the casing mechanism (controller of the ultrasound endoscope apparatus) according to the embodiment of the present invention and illustrate operation of the casing mechanism.
Figure 10:
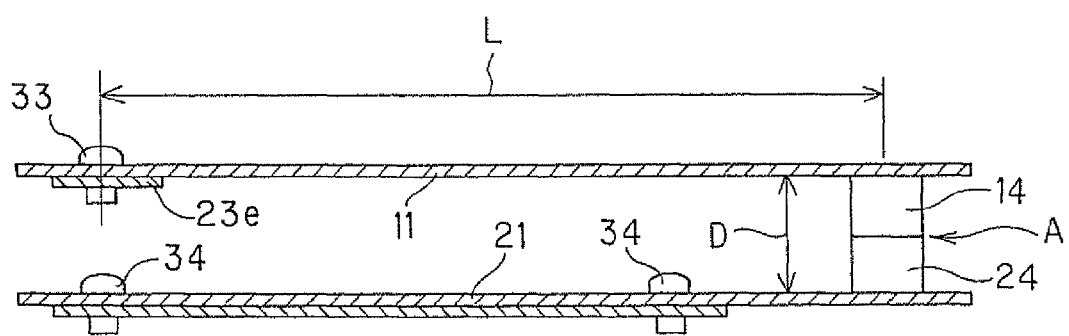
FIG. 10 is a conceptual diagram showing a cross section of the substrate unit in FIG. 9 when a circuit board is mounted securely on the substrate unit.
Figure 11:
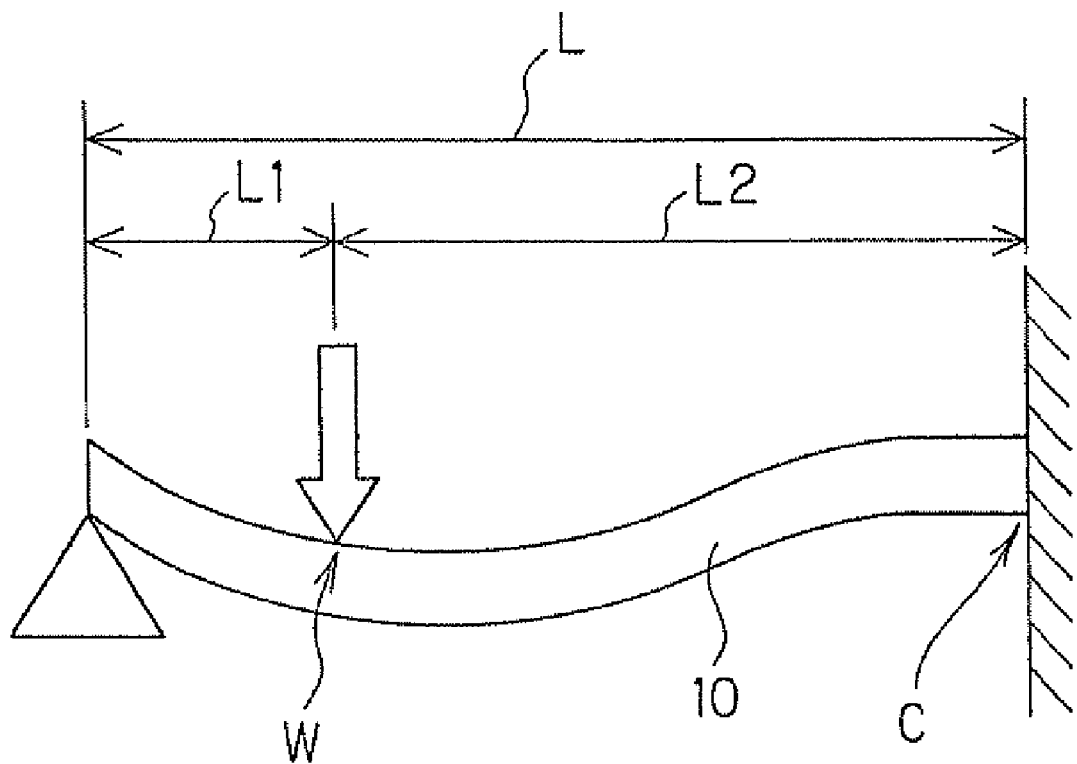
FIG. 11 is a conceptual diagram illustrating a load acting on a board mount in the casing mechanism according to the embodiment of the present invention.
Figure 12:
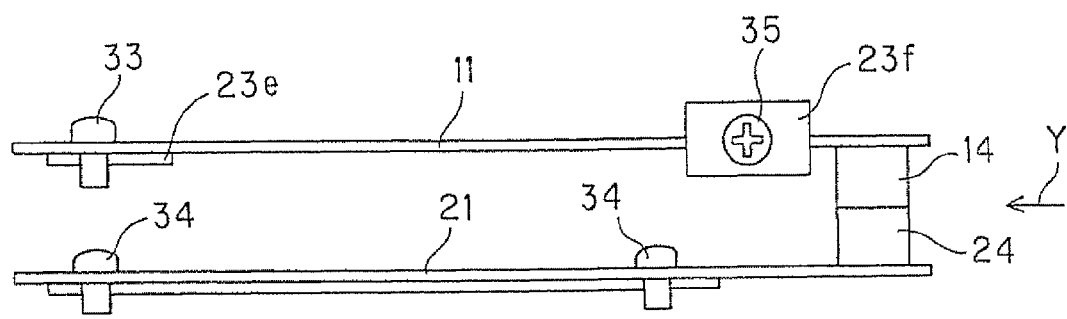
FIG. 12 is a conceptual diagram showing a flank of the casing mechanism in a state shown in FIG. 10.
Figure 13:
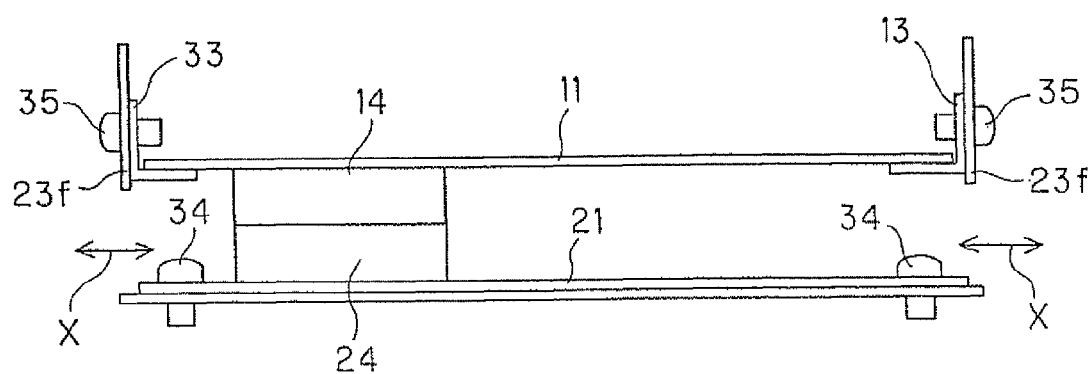
FIG. 13 is a conceptual diagram showing a front of the casing mechanism as viewed along arrow Y shown in FIG. 12.

FIGS. 9 to 13 are conceptual diagrams outlining assembly procedures of the casing mechanism (controller of the ultrasound endoscope apparatus) according to the present embodiment and illustrating operation of the casing mechanism. FIG. 9 is a conceptual diagram showing a cross section of one of substrate units in the casing mechanism according to the present embodiment. FIG. 10 is a conceptual diagram showing a cross section of the substrate unit in FIG. 9 when a circuit board is mounted securely on the substrate unit. FIG. 11 is a conceptual diagram illustrating a load acting on a board mount in the casing mechanism according to the present embodiment. FIG. 12 is a conceptual diagram showing a flank of the casing mechanism in a state shown in FIG. 10. FIG. 13 is a conceptual diagram showing a front of the casing mechanism as viewed along arrow Y shown in FIG. 12. Incidentally, FIG. 9 corresponds to a state shown in FIG. 3 while FIG. 10 corresponds to a state shown in FIG. 2. Thus, in FIGS. 9 to 13, the same components as those in FIGS. 1 to 8 are denoted by the same reference numerals as the corresponding components in FIGS. 1 to 8.

The present embodiment is an example in which the casing mechanism according to the present invention is applied to a casing of a controller of ultrasound endoscope apparatus which is a medical imaging apparatus. Therefore, before describing the present invention, a configuration of the ultrasound endoscope apparatus to which the present invention is applied will be outlined below.

As shown in FIG. 1, the ultrasound endoscope apparatus 1 to which the casing mechanism according to the present invention is applied mainly includes an ultrasound endoscope 2 equipped with an ultrasound transducer, an image pickup device, and the like; a controller 6 which controls the ultrasound endoscope 2 and performs various types of signal processing by receiving signals from the ultrasound endoscope 2; a light source 7 which supplies an illumination beam to the ultrasound endoscope 2; and a display apparatus 8 which displays ultrasound images, endoscopic images, and the like by receiving image signals acquired by the ultrasound endoscope 2 and processed by the controller 6.

The ultrasound endoscope 2 mainly includes a slender insertion portion 3 which is inserted into a body cavity, an operation portion 4 which, being continuous with a proximal end portion of the insertion portion 3, has various control members, and a universal cord 5 which extends form a flank of the operation portion 4.

An ultrasound transducer, an image pickup device such as a photoelectric conversion device, and the like are disposed in a distal end portion 3a of the insertion portion 3, where the ultrasound transducer transmits and receives ultrasound waves and the image pickup device performs photoelectric conversion by receiving an optical image of an object to be observed and examined. A signal line, mechanical member, light guide cable, and the like are passed through the insertion portion 3, where the signal line connects the ultrasound transducer, image pickup device, and the like in the distal end portion 3a with internal electric components in the operation portion 4, the mechanical member is used for bending operation of part around the distal end portion 3a of the insertion portion 3, and the light guide cable transmits the illumination beam.

The signal line and light guide cable passed through the insertion portion 3 are further passed through the operation portion 4, the universal cord 5, and then a connector unit 5a installed at one end of the universal cord 5.

The connector unit 5a of the universal cord 5 has multiple connecting portions connected with a coupling connector of a connection cable extending from the light source 7 and with a coupling connector of a connection cable extending from the controller 6.

The controller 6 mainly includes an ultrasound imaging unit 6a and a processor unit 6b, where the ultrasound imaging unit 6a controls driving of the ultrasound transducer and the like of the ultrasound endoscope 2 and performs various types of signal processing on an ultrasound signal from the ultrasound transducer of the ultrasound endoscope 2 while the processor unit 6b controls driving of the image pickup device of the ultrasound endoscope 2 and performs various types of signal processing on a video signal and the like acquired by the image pickup device 25 of the ultrasound endoscope 2.

The ultrasound imaging unit 6a and processor unit 6b of the controller 6 are pieces of electronic equipment, each of which are provided in the form of a board unit containing circuit boards and the like in a casing with various control circuits, signal processing circuits, and the like being mounted on the circuit boards.

The controller 6 is electrically connected with the display apparatus 8. The display apparatus 8 displays ultrasound images, endoscopic images, and the like by receiving the video signal outputted from the controller 6.

With the insertion portion 3 of the ultrasound endoscope 2 inserted in the body cavity of a subject, the ultrasound endoscope apparatus 1 configured as described above controls the ultrasound transducer and image pickup device in the distal end portion 3a by means of the controller 6 and thereby displays conditions of organs and the like in the body cavity in the form of ultrasound images or endoscopic images on the display apparatus 8. Then, a user carries out diagnosis and the like by observing the ultrasound images and endoscopic images displayed on the display apparatus 8.

The casing mechanism according to the present embodiment is applied to the controller 6 of the ultrasound endoscope apparatus 1 described above. Now, the casing mechanism of the controller 6 will be described below.

The controller 6 mainly includes the ultrasound imaging unit 6a and processor unit 6b as described above.

As shown in FIGS. 2 to 5, the ultrasound imaging unit 6a and processor unit 6b are configured as separate board units. The two board units (6a and 6b) are electrically interconnected via respective connector members 14 and 24 installed on the board units (see also FIG. 6).

Being electrically interconnected via the respective connector members 14 and 24, the two board units (6a and 6b) are fastened, with screws, to a board support 23c mounted on side plates 23a and 23b and the like, which are part of the casing members of the controller 6 as well as to fixing lugs 23e and 23f and the like (see FIGS. 2, 7, and 8).

As shown in FIG. 3, the processor unit 6b includes a first circuit board 21 on which a first connector member 24 is mounted, where the first circuit board 21 is the first circuit board, and the first connector member 24 is the first connector. The first circuit board 21 is fastened to the board support 23c mounted on the side plates 23a and 23b and the like, which are part of the casing members of the controller 6 with screws. The board unit which constitutes a major component of the processor unit 6b is configured in this way.

Incidentally, the first connector member 24 fits in a second connector member 14 (described later) to electrically interconnect the first circuit board 21 and a second circuit board 11. The first connector member 24 and second connector member 14 each have a large number (e.g., approximately a few hundred) of connection terminals, which corresponds to the number of ultrasound transducers of the ultrasound endoscope 2.

On the other hand, as shown in FIGS. 4 and 5, the ultrasound imaging unit 6a includes the second circuit board 11 on which the second connector member 14 is mounted, casing members (side plates 13 and bottom plate 13b) which hold the second circuit board 11 fixed, and a box-shaped lid member 16 which constitutes part of the casing members, being placed so as to cover top and side faces of the second circuit board 11, where the second connector member 14 is the second connector and the second circuit board 11 is the second circuit board.

According to the present embodiment, as shown in FIGS. 2, 6, and the like, the second connector member 14 is mounted on a relay board 12, which is connected electrically with the second circuit board 11 via connection means such as a connector (not shown). Consequently, the second connector member 14 is electrically connected with the second circuit board 11 via the relay board 12.

As shown in FIG. 5, the relay board 12 is placed on the outside of a lateral edge of the second circuit board 11, i.e., placed off a mounting surface of the second circuit board 11, and fastened in place to a part (side plates 13 or bottom plate 13b) of the casing members with screws (not shown).

With the relay board 12 mounted in place on the casing members, the mounting surfaces of the second circuit board 11 and relay board 12 are oriented perpendicular to each other. Terminals of the second connector member 14 are mounted in place, facing upward, on the mounting surface of the relay board 12.

The second circuit board 11 is fastened, with screws, to fasteners (not shown) which, being installed on a part (side plates 13 or bottom plate 13b) of the casing members, serve as a board support. In this state, the lid member 16 is disposed so as to cover the top and side faces of the second circuit board 11 while the lid member 16 and the bottom plate 13b of the casing members are fastened to each other with screws at predetermined locations.

The second circuit board 11 housed and fastened in inner space of the casing provide the board unit of the ultrasound imaging unit 6a, where the inner space of the casing is formed by a part (side plates 13 or bottom plate 13b) of the casing members and the lid member 16.

The board unit of the ultrasound imaging unit 6a is fixedly mounted in place on the support provided by the casing members of the controller 6.

In this case, with the second connector member 14 of the second circuit board 11 (relay board 12) and the first connector member 24 of the first circuit board 21 fitted together, the ultrasound imaging unit 6a is fastened in place to the casing members of the controller 6, i.e., to the fixing lugs 23e and 23f (see FIGS. 7 and 8), with screws.

Incidentally, as shown in FIG. 7, the fixing lug 23e is a nail-shaped part formed by bending predetermined part of the side plate 23a—which is part of the casing members of the controller 6—in such a way as to protrude outward from the side plate 23a in a direction approximately perpendicular to the side plate 23a. On the other hand, as shown in FIG. 8, the fixing lug 23f is a nail-shaped part formed by cutting predetermined part of the side plate 23a which is part of the casing members of the controller 6.

In this case, the fixing lugs 23e are disposed away from the first connector member 24 and second connector member 14 mounted on the first circuit board 21 and second circuit board 11 disposed in the casing members of the controller 6. The fixing lugs 23f are disposed close to the first connector member 24 and second connector member 14.

Threaded screw holes 23ea with thread grooves to screw respective screws 33 and 35 (see FIGS. 7 and 8) have been bored in both of fixing lug 23e and 23f.

In this case, the fixing lug 23e protrudes outward from the side plate 23a as described above. Thus, the screw 33 screwed into the screw hole 23ea bored in the fixing lug 23e is inserted along the side plate 23a, i.e., in a direction perpendicular to the controller 6.

As the screws 33 are screwed into the fixing lugs 23e via casing fasteners 13a of the ultrasound imaging unit 6a, the fixing lugs 23e fasten the board unit of the ultrasound imaging unit 6a to part of the casing members of the controller 6.

The casing fasteners 13a of the ultrasound imaging unit 6a are formed in predetermined locations of the side plates 13 which are part of the casing members of the ultrasound imaging unit 6a (which is a board unit), i.e., in such locations as to overlap the fixing lugs 23e of the controller 6 when the ultrasound imaging unit 6a is mounted in place in the controller 6.

The casing fasteners 13a are nail-shaped parts formed by bending predetermined part of the side plates 13—which are formed, for example, by sheet metal working—in such a way as to protrude outward from the side plate 23a in a direction approximately perpendicular to the side plates 13. A through-hole large enough to pass the screw 33 has been formed in each casing fastener 13a. The through-hole is made slightly larger in diameter than the screw 33 to make some allowance. This is done to absorb misalignment between the through-holes in the casing fasteners 13a and screw holes 23ea in the fixing lugs 23e when the ultrasound imaging unit 6a is put in place in the controller 6.

Specifically, the allowance made in the through-holes in the casing fasteners 13a allows the casing fasteners 13a to function as stress absorbing means which absorbs stresses produced in the two connector members 14 and 24 as a result of misalignment between the through-holes in the casing fasteners 13a and screw holes 23ea in the fixing lugs 23e when the casing fasteners 13a are fastened to the fixing lugs 23e with the ultrasound imaging unit 6a (second circuit board 11) put in place in the controller 6.

On the other hand, as described above, the fixing lug 23f is formed by cutting part of the side plate 23a. That is, the fixing lug 23f is formed along the side plate 23a. A through-hole for the fixing screw 35 to pass through is formed in the fixing lug 23f. Thus, the screw 35 passed through the through-hole of the fixing lug 23f is oriented in a direction perpendicular to the side plate 23a, i.e., in a direction parallel to a plane of the controller 6.

Consequently, the fixing lugs 23f are disposed in such locations as to approximately coincide with screw holes 13c in the side plates 13 of the ultrasound imaging unit 6a when the ultrasound imaging unit 6a (second circuit board 11) is put in place in the controller 6 with the first connector member 24 and second connector member 14 interconnected.

The fixing lug 23f, which is formed by cutting the side plate 23a, is formed elastically so that the distal end portion can move in directions perpendicular to the side plate 23a, i.e., in directions along a plane of the second circuit board 11 in the ultrasound imaging unit 6a (board unit), with the proximal end portion supported.

That is, the casing of the controller 6 according to the present embodiment is formed by sheet metal working, and thus the side plate 23a is formed by sheet metal working as well. Consequently, the fixing lug 23f formed by cutting the side plate 23a has elasticity.

Furthermore, a notch 23fa is formed in the proximal end portion of the fixing lug 23f. The notch 23fa is provided to facilitate elastic deformation of the fixing lug 23f.

The fixing lugs 23f, which are part of the side plates 23a and 23b, are designed to be deformed when the screws 35 passed through the through-holes in the fixing lugs 23f are tightened by being screwed into screw holes 13c in the side plates 13 of the ultrasound imaging unit 6a after the ultrasound imaging unit 6a (second circuit board 11) is put in place in the controller 6 with the first connector member 24 and second connector member 14 interconnected. This makes it possible to fasten the board unit of the ultrasound imaging unit 6a to the casing members (side plates 23a and 23b) of the controller 6 without imposing loads on the connector members 14 and 24 or the board unit.

Incidentally, if size of the notch 23fa is varied as required, elastic force of the fixing lug 23f can be set to a desired level.

Depending on size setting of the notch 23fa, the fixing lug 23f can be formed as a part having plasticity. Also, depending on what material is selected for the side plate 23a, the fixing lug 23f can be configured to be either elastic or plastic as desired.

Figure 14:
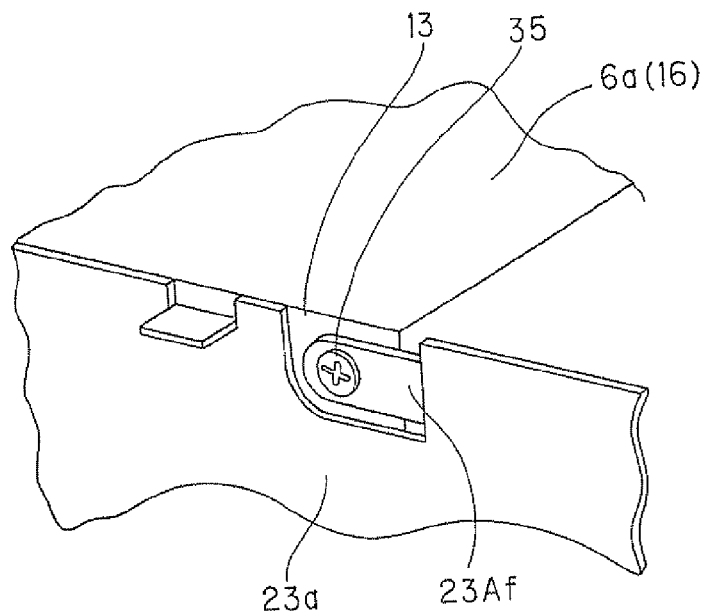
FIG. 14 is an enlarged perspective view showing principal part of a variation of a fixing lug located near a connector member in the casing mechanism according to the embodiment of the present invention.

Alternatively, as exemplified by a variation shown in FIG. 14, a fixing lug 23Af may be made of a plate material with a high elastic modulus and disposed integrally in a predetermined part of the side plate 23a.

The fixing lugs 23f thus configured to be either elastic or plastic function as stress absorbing means which absorbs stresses in a plane direction of the two connector members 14 and 24 by means of elasticity or plasticity when the ultrasound imaging unit 6a is fixedly mounted using the fixing lugs 23f after the ultrasound imaging unit 6a (second circuit board 11) is put in place in the controller 6 with the first connector member 24 and second connector member 14 interconnected.

Being configured as described above, the casing mechanism according to the present embodiment is applied to the controller 6 of the ultrasound endoscope apparatus 1. Now, brief assembly procedures and operation of the controller 6 of the ultrasound endoscope apparatus 1 will be described below with reference to FIGS. 9 to 13. Besides, FIGS. 1 to 8 will also be referred to as required.

First, as shown in FIGS. 3 and 9, the first circuit board 21 is fastened to the board support 23c of the casing side with screws 34 in multiple places.

Next, the first connector member 24 of the first circuit board 21 fastened to the casing members is fitted in the second connector member 14 of the ultrasound imaging unit 6a which is a board unit containing the second circuit board 11. This ensures electrically stable connection between the first circuit board 21 and the board unit containing the second circuit board 11.

In this state, the board unit containing the second circuit board 11 is fastened to predetermined part of the casing members, i.e., to the fixing lugs 23e and 23f, with screws.

In this case, first the board unit is fastened to the fixing lugs 23e located away from the connector members 14 and 24 (by a distance of L; see FIG. 10).

That is, after the two circuit boards 11 and 21 are fastened through a fit between the connector members 14 and 24, the second circuit board 11 and the fixing lugs 23e on the casing members are fastened with screws first at locations away from fastening position, i.e., away from the connector members 14 and 24, making it possible to reduce loads acting on the connector members 14 and 24 even if there is an error in board-to-board distance between the two circuit boards 11 and 21.

Now, the load acting on the board mount of the casing mechanism according to the present embodiment will be described with reference to the conceptual diagram in FIG. 11.

As shown in FIG. 11, it is assumed that a total length of a circuit board or a board unit (hereinafter referred to as a circuit board or the like) 10, for example, is L and that one end denoted by C is fixedly supported by a connector member. In this case, it is assumed that the circuit board or the like 10 is fastened at a predetermined spot on the circuit board or the like 10, i.e., at a spot denoted by W.

Also, it is assumed that distance from position A on the connector member to a fastening spot W of the circuit board or the like 10 is L2 and that distance from the fastening spot W to the other end of the circuit board or the like 10 is L1.

In this case, the load (stress) acting on the fastening spot W of the circuit board or the like 10 is given by Equation (1) below.

[Formula 1]

$$\sigma_{max}(X = L1) = \frac{Mmax}{Z} \qquad (1)$$
$$= \frac{1}{2} \cdot W \cdot L1 \cdot L2^2 \cdot \frac{(3 \cdot L1 + 2 \cdot L2)}{(L^3 \cdot Z)}$$

where
σmax: maximum bending stress (kg/mm²)
I: geometric moment of inertia (mm⁴)
Mmax: bending moment (kg·cm)
Z: section modulus (mm³)
W: weight (kg)
L: beam length (mm)
L1: beam length from one end to point of application of weight (mm)
L2: beam length from the other end to the point of application of weight (mm)

Thus, for example, if L1>L2, it is self-evident from Equation (1) that the load (stress) acting on the fastening spot W can be reduced.

Specifically, for example, if a fixing lug formed by sheet metal working measures 12 mm wide and 1 mm thick and set dimensions of the circuit board or the like 10 are L=100, L1=10, and L2=90, it follows from Equation (1) that the maximum stress σmax at the fastening spot W is 4.25 kg/mm³.

On the other hand, if the set dimensions of the circuit board or the like 10 are L=100, L1=90, and L2=10, then the maximum stress σmax=0.65 kg/mm³.

It can be seen that the stress in the latter example is one sixth (⅙) the stress in the former example.

Thus, according to the present embodiment, when mounting the ultrasound imaging unit 6a—which is the board unit containing the second circuit board 11—on the fixing lugs 23e, by fastening the ultrasound imaging unit 6a at locations as far away from the connector members 14 and 24 as possible, it is possible to reduce the loads acting on the circuit board or board unit (the ultrasound imaging unit 6a) even if there is an error in the board-to-board distance.

On the other hand, near the connector members 14 and 24, the board unit containing the second circuit board 11 is fastened to the fixing lugs 23f of the casing members with screws as described above. That is, the board unit is mounted and fastened to the side plates 13 of the casing members via the fixing lugs 23f in directions along the plane of the second circuit board 11 (see FIGS. 12 and 13).

In this case, to absorb mounting errors in directions along the plane of the second circuit board 11, the fixing lugs 23f are formed so as to deform elastically in directions of arrows X in FIG. 13. This makes it possible to mount and fasten the board unit without imposing loads on the connector members 14 and 24 even if there are mounting errors in directions along the plane of the second circuit board 11.

As described above, according to the present embodiment, the casing mechanism used to mount and fasten circuit boards and board units in the casing makes it possible to mount and fasten the ultrasound imaging unit 6a (board unit) to the casing mechanism reliably by maintaining proper positioning and efficient member layout without impairing workability or imposing loads on the ultrasound imaging unit 6a (board unit) while ensuring electrical connection between the ultrasound imaging unit 6a (board unit) and the second circuit board 11 by means of the connector members 14 and 24, where the ultrasound imaging unit 6a (board unit) is equipped with the first circuit board 21 which has a large number of connection pins and handles weak signals as in the case of the controller 6 of the ultrasound endoscope apparatus 1.

In this case, at locations away from the connector members 14 and 24, by fastening the circuit board with screws in a direction approximately perpendicular to the plane of the circuit board, it is possible to absorb mounting errors in directions along the plane of the circuit board. On the other hand, near the connector members 14 and 24, by fastening the circuit board with screws in a direction along the plane of the circuit board and making the fixing lugs 23f elastically deformable in the same direction, it is possible to absorb mounting errors in directions perpendicular to the plane of the circuit board.

In the embodiment described above, the fixing lug 23f formed by cutting part of the side plate 23a made of sheet metal working has been cited as a configuration example of the fixing lugs of the controller 6 of the ultrasound endoscope apparatus 1, i.e., the fixing lugs disposed near the connector members 14 and 24. Also, a plate-like fixing lug 23Af formed separately from the side plate 23a has been cited as a variation of the fixing lug 23f. Both fixing lugs 23f and 23Af absorb mounting errors using elastic deformation.

Figure 15:
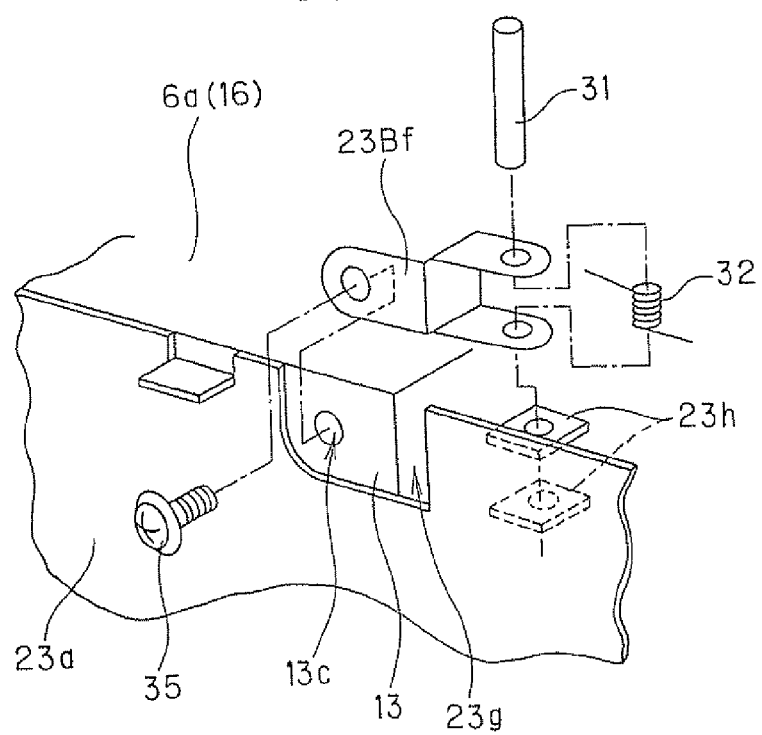
FIG. 15, which shows a second variation of the casing mechanism according to the embodiment of the present invention, is an enlarged exploded perspective view showing principal part in another configuration example of the fixing lug disposed near the connector member in the controller of the ultrasound endoscope apparatus.

However, forms of fixing lug disposed near the connector members 14 and 24 are not limited to the above examples, and a form shown in FIG. 15 is also conceivable.

FIG. 15, which shows a second variation of the casing mechanism according to the embodiment of the present invention, is an enlarged exploded perspective view showing principal part in another configuration example of the fixing lug disposed near the connector member in the controller of the ultrasound endoscope apparatus.

As shown in FIG. 15, the fixing lug 23Bf according to the present variation is formed separately from the side plate 23a in such a way as to be movable from a flank of the ultrasound imaging unit 6a (board unit) in a direction along the plane of the circuit board.

The fixing lug 23Bf has a nail-shaped part with a through-hole for the screw 35 to pass through. The nail-shaped part has base-side strips at the base, each with a through-hole for a support shaft 31 to pass through in a direction approximately perpendicular to a direction of passage of the screw 35. The nail-shaped part of the fixing lug 23Bf is placed in a recess 23g in the side plate 23a.

On the other hand, base plates 23h are installed on the inside of the side plate 23a, protruding inward, and a through-hole is bored in each base plate 23h to pass the support shaft 31. The base-side strips of the fixing lug 23Bf are placed on the base plates 23h. In this state, the support shaft 31 is passed through the through-holes in the base plates 23h and base-side strips. Furthermore, an urging member 32 such as a coil spring is wound around the support shaft 31. The urging member 32 urges the nail-shaped part of the fixing lug 23Bf either toward or away from the ultrasound imaging unit 6a. Consequently, the fixing lug 23Bf is disposed in such a way as to be pivotable in relation to the side plate 23a in directions approximately perpendicular to wall surfaces of the side plate 23a.

After the ultrasound imaging unit 6a (second circuit board 11) is put in place in the controller 6 with the first connector member 24 and second connector member 14 (neither is shown; see the above embodiment) interconnected, when the screw 35 is passed through the through-hole in the fixing lug 23Bf and is tightened by being screwed into the screw hole 13c in the side plate 13 of the ultrasound imaging unit 6a, the nail-shaped part of the fixing lug 23Bf is mounted on the ultrasound imaging unit 6a. The fixing lug 23Bf becomes locally deformed with respect to the side plate 23a by urging force of the urging member 32 and thereby absorbs mounting errors in the directions along the plane of the ultrasound imaging unit 6a (second circuit board 11 in the board unit).

According to the present variation, the fixing lug 23Bf is formed separately from the side plate 23a in such a way as to be pivotable in relation to the side plate 23a and urged in a predetermined direction by the urging force of the urging member 32, making it possible to extend a range in which the mounting errors in the directions along the plane of the ultrasound imaging unit 6a (second circuit board 11 in the board unit) can be absorbed.

Figure 16:
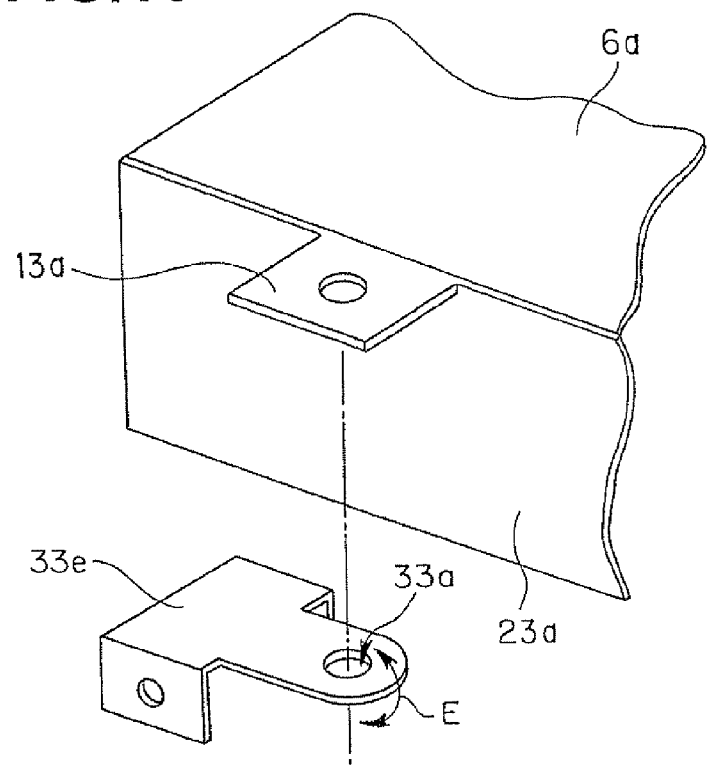
FIG. 16 is an enlarged exploded perspective view showing principal part of another form of fixing lug located away from the connector member in another variation of the casing mechanism according to the embodiment of the present invention.
Figure 17:
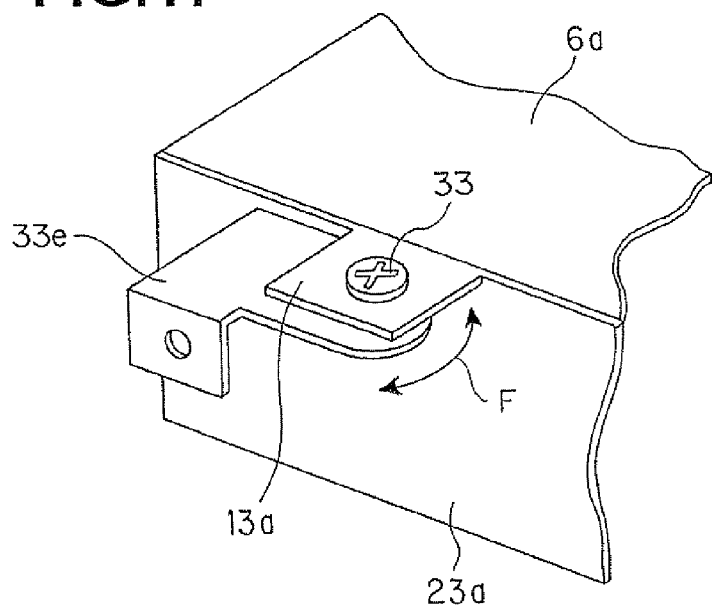
FIG. 17 is an enlarged perspective view showing the principal part of the variation in FIG. 16 after assembly.
Figure 18:
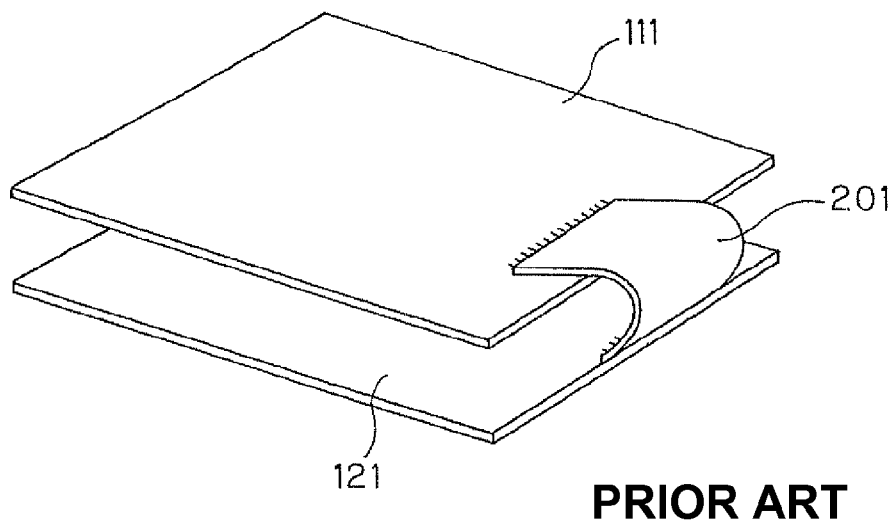
FIG. 18 is a diagram showing an example in which multiple circuit boards in conventional electronic equipment are interconnected by a wire harness.
Figure 19:
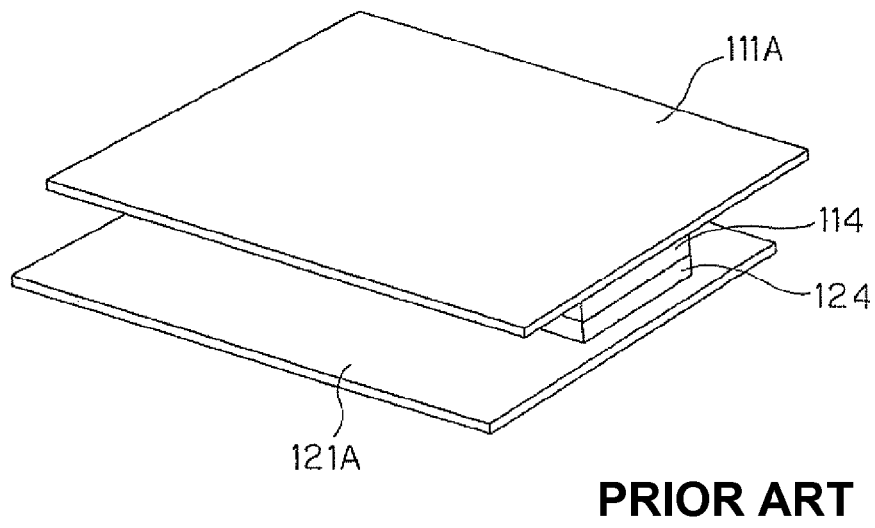
FIG. 19 is a diagram showing an example in which multiple circuit boards in conventional electronic equipment are interconnected by connector members mounted on the circuit boards.
Figure 20:
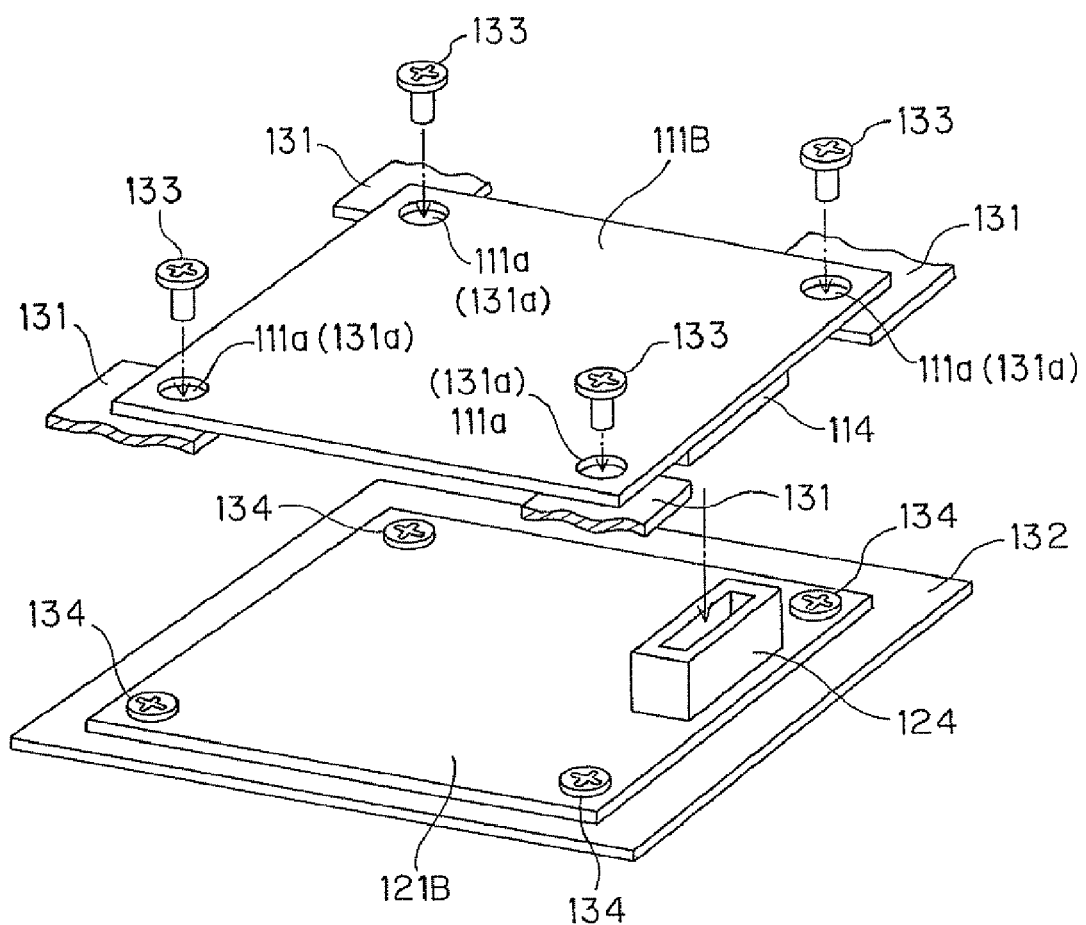
FIG. 20 is a diagram showing a concrete configuration of a casing mechanism structured to electrically interconnect circuit boards, board units, and the like using connector members installed on the circuit boards and fasten the circuit boards and the like to casing fasteners with screws, in electronic equipment of a conventional medical imaging apparatus.

On the other hand, FIGS. 16 and 17 show another variation of the fixing lug located away from the connector members 14 and 24. FIG. 16 is an enlarged exploded perspective view of principal part and FIG. 17 is an enlarged perspective view of the principal part after assembly.

In the embodiment described above, the fixing lug 23e located away from the connector members 14 and 24 is formed integrally with the side plate 23a by bending a predetermined part of the side plate 23a. According to the present variation, separate fixing lug 33e is mounted on the side plate 23a instead of the fixing lug 23e.

The fixing lug 33e has a screw hole 33a, a nail-shaped part which has elasticity in directions of arrow E in FIG. 16, and a base fixedly mounted on the side plate 23a. The screw 33 passed through the through-hole in the casing fastener 13a is screwed into the fixing lug 33e fixedly mounted on a predetermined part of the side plate 23a via the base. Consequently, the casing fastener 13a of the ultrasound imaging unit 6a is mounted in such a way as to be swingable in relation to the fixing lug 33e in directions of arrow F in FIG. 17, i.e., in directions along the plane of the ultrasound imaging unit 6a (the second circuit board 11 in the ultrasound imaging unit 6a).

This allows the fixing lug 33e to absorb mounting errors in directions perpendicular to the plane of the ultrasound imaging unit 6a (second circuit board 11 in the board unit) (i.e., in the directions of arrow E in FIG. 16) using the elasticity of the nail-shaped part. Also, since the ultrasound imaging unit 6a is swingable in relation to the fixing lug 33e in directions along the plane of the ultrasound imaging unit 6a (i.e., in the directions of arrow F in FIG. 17), it is possible to absorb mounting errors in the directions along the plane of the ultrasound imaging unit 6a.

The present invention is not limited to the embodiment described above, and various modifications and applications are possible without departing from the spirit of the present invention.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A casing mechanism comprising:
   a casing;
   a board support provided to the casing, and to which a first circuit board on which a first connector is mounted is fastened with a screw;
   stress absorbing means provided to the casing, for fastening with a screw a second circuit board on which a second connector for connection to the first connector is mounted, in a state where the first connector and the second connector are connected to each other,
   wherein the stress absorbing means comprises:
      a first fixing lug including a screw hole perpendicular to a plane direction of the first circuit board; and
      a second fixing lug provided at a position closer to the first connector and the second connector than to the first fixing lug, the second fixing lug having elasticity so that the second fixing lug can move in the plane direction of the first circuit board and having a screw hole in the same direction as the plane direction of the first circuit board.

2. The casing mechanism according to claim 1, wherein the second fixing lug is formed by cutting a part of the casing.

3. The casing mechanism according to claim 1, wherein the second fixing lug is formed with a separate part having an elasticity factor larger than that of the casing and is disposed integrally to the casing.

4. The casing mechanism according to claim 1, wherein the second fixing lug is constituted by another part other than the casing and is disposed rotatably around a support shaft perpendicular to the plane direction of the first circuit board.

5. A medical imaging apparatus comprising a casing mechanism, wherein the casing mechanism includes:
a casing;
a board support provided to the casing, and to which a first circuit board on which a first connector is mounted is fastened with a screw;
stress absorbing means provided to the casing, for fastening with a screw a second circuit board on which a second connector for connection to the first connector is mounted, in a state where the first connector and the second connector are connected to each other,
wherein the stress absorbing means comprises:
a first fixing lug including a screw hole perpendicular to a plane direction of the first circuit board; and
a second fixing lug provided at a position closer to the first connector and the second connector than to the first fixing lug, the second fixing lug having elasticity so that the second fixing lug can move in the plane direction of the first circuit board and having a screw hole in the same direction as the plane direction of the first circuit board.

6. The medical imaging apparatus according to claim 5, wherein the second fixing lug is formed by cutting a part of the casing.

7. The medical imaging apparatus according to claim 5, wherein the second fixing lug is formed with a separate part having an elasticity factor larger than that of the casing and is disposed integrally to the casing.

8. The medical imaging apparatus according to claim 5, wherein the second fixing lug is constituted by another part other than the casing and is disposed rotatably around a support shaft perpendicular to the plane direction of the first circuit board.

9. An ultrasound endoscope comprising a casing mechanism, wherein the casing mechanism includes:
a casing;
a board support provided to the casing, and to which a first circuit board on which a first connector is mounted is fastened with a screw;
stress absorbing means provided to the casing, for fastening with a screw a second circuit board on which a second connector for connection to the first connector is mounted, in a state where the first connector and the second connector are connected to each other,
wherein the stress absorbing means comprises:
a first fixing lug including a screw hole perpendicular to a plane direction of the first circuit board; and
a second fixing lug provided at a position closer to the first connector and the second connector than to the first fixing lug, the second fixing lug having elasticity so that the second fixing lug can move in the plane direction of the first circuit board and having a screw hole in the same direction as the plane direction of the first circuit board.

10. The ultrasound endoscope according to claim 9, wherein the second fixing lug is formed by cutting a part of the casing.

11. The ultrasound endoscope according to claim 9, wherein the second fixing lug is formed with a separate part having an elasticity factor larger than that of the casing, and is disposed integrally to the casing.

12. The ultrasound endoscope according to claim 9, wherein the second fixing lug is constituted by another part other than the casing and is disposed rotatably around a support shaft perpendicular to the plane direction of the first circuit board.

* * * * *